US008919340B2

(12) United States Patent
Blum

(10) Patent No.: US 8,919,340 B2
(45) Date of Patent: Dec. 30, 2014

(54) HAND-HELD POTASSIUM SUPER OXIDE OXYGEN GENERATING APPARATUS

(76) Inventor: Mel Blum, Wantagh, NY (US)

( * ) Notice: Subject to any disclaimer, the term of this patent is extended or adjusted under 35 U.S.C. 154(b) by 527 days.

(21) Appl. No.: 13/426,953

(22) Filed: Mar. 22, 2012

(65) Prior Publication Data

US 2013/0247908 A1 Sep. 26, 2013

(51) Int. Cl.
*A61M 11/00* (2006.01)

(52) U.S. Cl.
USPC ............. 128/202.26; 128/200.24; 128/204.22

(58) Field of Classification Search
CPC .......... A62B 7/08; A62B 21/00; A61M 16/10
USPC ............. 128/200.24, 202.12, 202.21, 202.26, 128/204.22, 205.26
See application file for complete search history.

(56) References Cited

U.S. PATENT DOCUMENTS

| | | | |
|---|---|---|---|
| 3,202,150 | A | 8/1965 | Miller |
| 3,702,110 | A | 11/1972 | Hoffman et al. |
| 3,860,396 | A | 1/1975 | Finley |
| 3,938,512 | A | 2/1976 | Mausteller et al. |
| 3,942,524 | A | 3/1976 | Li et al. |
| 4,265,238 | A | 5/1981 | Swiatosz et al. |
| 4,325,364 | A | 4/1982 | Evans |
| 5,267,558 | A | 12/1993 | Haertle et al. |
| 5,620,664 | A | 4/1997 | Palmer |
| 5,690,099 | A | 11/1997 | Abramov et al. |
| 6,957,651 | B2 | 10/2005 | Nuckols et al. |
| 7,513,251 | B2 | 4/2009 | Blum |

*Primary Examiner* — Steven Douglas
(74) *Attorney, Agent, or Firm* — Oliff PLC

(57) ABSTRACT

An oxygen generating apparatus that includes a container containing potassium super oxide, an inhale valve, and an inhale valve filter between the potassium super oxide and the inhale valve. The filter is configured to prevent particles having a diameter of 10 μm from passing through the filter, and to neutralize KOH and $KO_2$ particles having a diameter of less than 10 μm that contact the filter into a food grade compound.

20 Claims, 2 Drawing Sheets

HAND-HELD POTASSIUM SUPER OXIDE OXYGEN GENERATING APPARATUS

BACKGROUND

Emergency breathing apparatuses that provide oxygen to a user are known. Some provide oxygen directly, such as those that employ compressed or liquid oxygen. Others provide oxygen through a chemical reaction.

Conventional chemical oxygen generators may contain alkali metal chlorate candles, which are burned to produce oxygen. Other conventional chemical oxygen generators may contain potassium super oxide, which reacts with carbon dioxide to produce oxygen. Conventional chemical oxygen generators are generally used by miners, firefighters, military personal, and the like to provide emergency oxygen when needed.

For example, U.S. Pat. No. 5,690,099 to Abramov et al. discloses a closed-circuit breathing system that includes a mask and a canister containing, for example, $KO_2$. The canister contains one or more working compounds formed of a peroxide and/or superoxide of one or more metals of the alkali and alkaline-earth metal groups, such as $KO_2$ and $CaO_2$, and a moisture releasing material, such as wetted activated charcoal, is used to replenish the oxygen and absorb the carbon dioxide in exhaled air. The canister includes an inlet port for receiving exhaled air, and an outlet port for providing breathable air for inhalation. The patent describes that the canister can be used in a closed or semi-closed circuit breathing system worn by a user such as a fireman, miner etc.

U.S. Pat. No. 3,938,512 to Mausteller et al. discloses an emergency breathing apparatus that includes a mask having a breathing opening, directly in front of the outer end of which there is a chemical cartridge that is secured to the mask. The cartridge has an exhalation passage extending through it from front to back, with its rear end registering with the breathing opening. A check valve in the inhalation passage allows air flow only into the mask. In the exhalation passage there is a carbon dioxide removing and oxygen generating chemical. A breathing bag is supported by the cartridge and communicates with the front end of the exhalation passage. The mask is provided with an inhalation check valve allowing air being inhaled from the bag to bypass the chemical.

U.S. Pat. No. 5,267,558 to Haertle et al. discloses a chemical cartridge for respirators, the cartridge containing a chemical, e.g., potassium hyperoxide, which when acted upon by carbon dioxide and moisture, produces oxygen from a stream of inhaled air. Two discharge nozzles are provided that project into the chemical and out of which the regenerated exhaled air flows. The incoming flow occurs over a large area and the outflow occurs over a small area with the peripheral surfaces of the discharge nozzles being spaced substantially equidistant from an inlet surface of the chemical, thereby ensuring optimum use of the chemical for oxygen production purposes because a user's exhaled air is caused to flow completely through the entire space occupied by the chemical.

U.S. Pat. No. 3,942,524 to Li et al. discloses an emergency breathing apparatus that includes a canister containing layers of $KO_2$ particles separated by parallel screen assemblies, the upper two screen assemblies being connected by a vertical bypass screen near the canister inlet. The layered $KO_2$ bed is effective to remove $CO_2$ from exhaled breath, and generate oxygen for recharging the air prior to inhalation. The canister inlet is connected by a flexible hose to the exhalation side of a breather mouthpiece, the inhalation side of the mouthpiece being connected to the upper end of the inhalation chimney. Communication between the canister outlet and the lower end of the inhalation chimney is provided by a breather bag, fitted with a set of baffles to define a tortuous flow path for cooling the processed air. A collector mounted at the canister outlet prevents liquid $KO_2$ (which forms KOH) from entering the breather bag. To protect the user and confine the heat within the canister, the canister is insulated.

U.S. Pat. No. 3,860,396 to Finley discloses a light-weight, portable oxygen generator containing an alkali metal chlorate candle. The generator includes a generally tubular housing, preferably formed of extruded aluminum or other heat-conducting metal, and preferably includes longitudinally-extending ribs which serve to dissipate heat generated inside of the housing. The generator also includes a dispensing valve through which oxygen passes.

U.S. Pat. No. 5,620,664 to Palmer discloses a light-weight, personal, portable oxygen dispenser that includes a cylindrical body. The cylindrical body is a light-weight material, such as extrudable aluminum, with a fluted or ridged exterior configuration to minimize heat conductivity to the fingers of someone holding the dispenser while it is operating.

U.S. Pat. No. 4,325,364 to Evans discloses a training breathing apparatus that includes a disposable canister filled with a reagent that creates heat by reacting with the moisture in exhaled breath.

Despite these various designs, conventional portable oxygen generators pose substantial drawbacks that either limit their use, or limit their use by a wide range of individuals that otherwise could benefit from their use. For example, professionals that are used to using such portable oxygen generators are constrained by the weight, material quality, construction, or heat generation of such devices. Likewise, these issues of weight, quality, construction, and heat generation also tend to prohibit such oxygen generators from being used by non-professionals, such as athletes or the like. Moreover, many of the conventional oxygen generators cannot be transported on commercial aircraft due to potential safety problems and leakage from cabin air pressure. The present disclosure thus seeks to overcome these disadvantages of the prior art, and provide improved portable oxygen generators.

For example, conventional potassium super oxide oxygen generators are generally bulky and must be worn in a harness. Furthermore, the chamber in which the active ingredient is held is usually made from heavy, high grade stainless steel. For example, conventional potassium super oxide oxygen generators can weigh between 4.5 to 7.5 kg.

U.S. Pat. No. 7,513,251 discloses a potassium super oxide oxygen apparatuses in which the oxygen reaction is slowed down to decrease heat generation, thereby allowing the apparatus to be hand-held. Such hand-held generators may be used by, for example, people escaping fires, skiers, mountain climbers, asthmatics, people with emphysema, people suffering from altitude sickness, and athletes. Such hand-held generators may be also used as backup oxygen generators for Emergency Medical Service (EMS) squads, fire departments, miners, and the like, should their regular emergency oxygen become depleted.

SUMMARY

It has now been discovered that very fine particles of $KO_2$ may be produced from granular, pellets, or sheets of potassium super oxide material used in oxygen generator devices such as those disclosed in U.S. Pat. No. 7,513,251. Vigorous handling or shaking of such devices, poor quality granular, pellets, or sheets of $KO_2$, or a breakdown of the $KO_2$ granules over prolonged periods of time may result in creating some fine powder that may be potentially absorbed by the user. It was also discovered during actual usage that the $KO_2$ also partially reverts to the highly caustic KOH.

BRIEF DESCRIPTION OF THE DRAWINGS

Various embodiments will be described in detail, with reference to the following figures, wherein.

DETAILED DESCRIPTION OF EMBODIMENTS

Figure 1A:
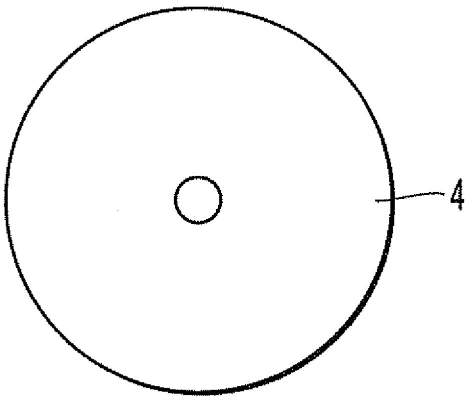
FIG. 1A illustrates a graphite or carbon fiber fabric.
Figure 1B:
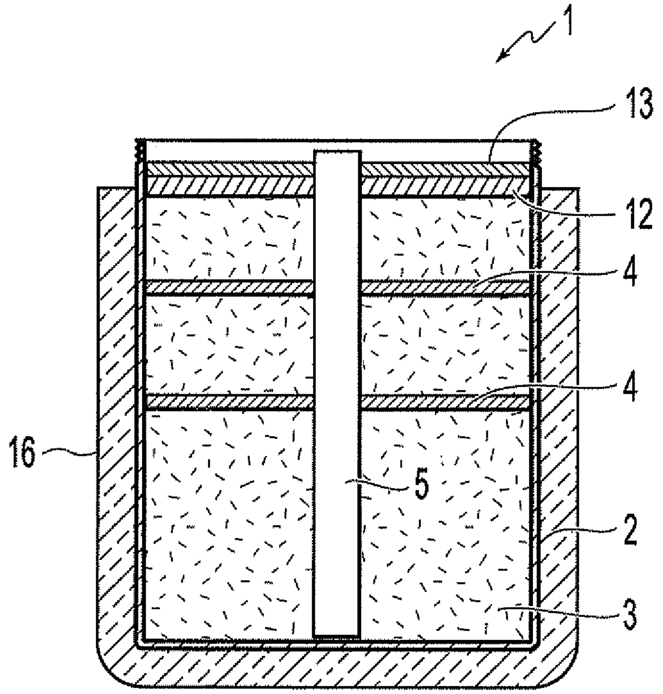
FIG. 1B illustrates an oxygen generating and breathing apparatus incorporating the fabric.
Figure 2A:
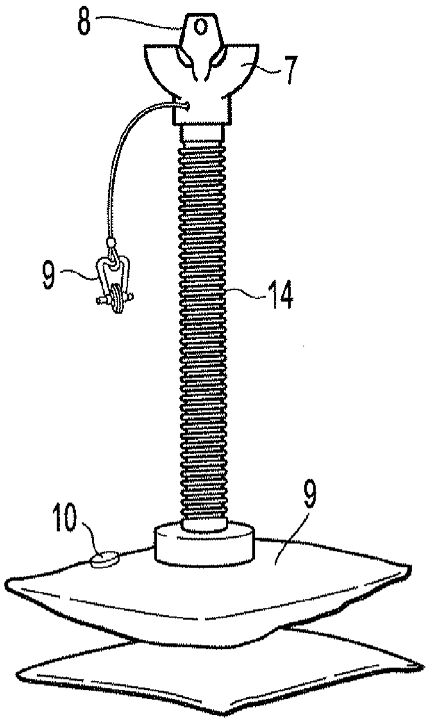
FIGS. 2A-2C illustrate embodiments of a mask and a mouth piece.
Figure 2B:
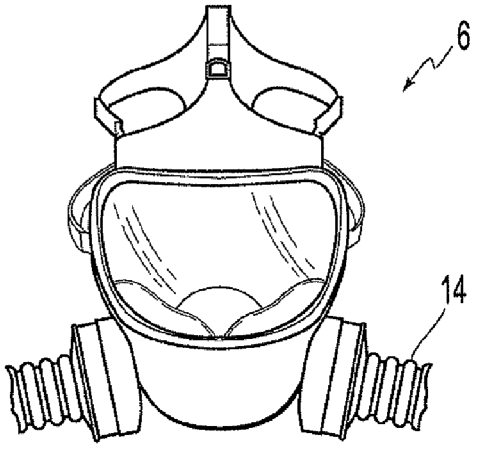
Figure 2C:
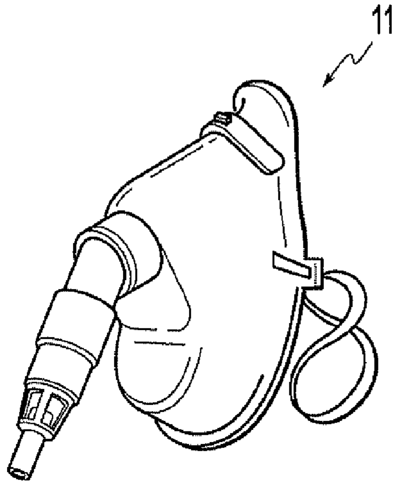

This disclosure is directed to a portable, light-weight, hand-held oxygen generating and breathing apparatus. As one breathes into the apparatus, the carbon dioxide and moisture from the breath react with potassium super oxide contained within the apparatus, thus liberating heat and warm dry oxygen. As illustrated in FIGS. 1B and 2, the apparatus (1) may include a mask (6) or (11) or a mouth piece (7), a container (2) containing potassium super oxide (3), one or more graphite or carbon fiber fabrics (4), an inhale filter (13), and an inhale valve (12) that regulates oxygen flow.

The container may be made of aluminum or other light-weight metal. For example, other suitable metals that may be used to form the container include aluminum alloys, magnesium, tin, thin wall steel (such as stainless steel and carbon steel), and the like. Aluminum is preferred in terms of its light weight, and spray coated or anodized aluminum is preferred over plain aluminum, which can potentially react with KOH in solution. Other metals may be used depending upon the size of the container and its intended use. For example, where the container is expected to be relatively small, the selection of a specific metal may be less important because the weight of the metal becomes less of a concern. Alternatively, the container may be made of ceramics, fiber glass, tempered (shatter-proof) glass, and TEFLON®.

The interior of the container may be coated with an inert polymer so that the active ingredients inside of the container do not react with the container. For example, various chemical-resistant coatings are known in the art, and can readily be incorporated into a protective coating layer primarily for the inside of the container. Suitable chemical-resistant coatings include, but are not limited to, halogenated materials such as HALAR® ethylene-chlorotrifluoro ethylene copolymer (ECTFE) (Allied Chemical Corporation, Morristown, N.J.), TEFZEL® ethylene-tetrafluoroethylene (ETFE) (E.I. duPont de Nemours and Co. Wilmington, Del.), tetrafluoroethylene (TFE), TEFLON® polytetrafluoroethylene (PTFE), polytetrafluoroethylene fluorinated ethylene propylene (PTFE-FEP), polytetrafluoroethylene perfluoroalkoxy (PTFE-PFA), polyvinylidene fluoride (PVDF), polyethylene, polypropylene, and the like. TEFLON® (polytetrafluoroethylene or PTFE) is particularly preferred, in terms of its chemical properties and ready commercial availability.

The container may be jacketed with an insulating and/or heat-dissipating jacket (16). The insulating jacket may be made of, for example, silicone rubber, a meta-aramid polymer such as NOMEX® duPont de Nemours and Co. Wilmington, Del.), thick cotton fabric, fabrics treated with phosphate, or other insulating materials. The insulating jacket may be ribbed (not shown) on the inside surface, on the outside surface, or on both of the inside and the outside surfaces. Such ribs may be helpful, for example, in further insulating the user from heat generated inside the container, by providing a decreased surface area for heat to transfer from the container wall, to the insulating jacket, and thereafter to the user. Alternatively, or in addition, the container can include a heat-dissipating jacket to remove some of the heat generated within the container while not transferring that heat to the user. The container may optionally include a connector for more convenient use. For example, the container may include a lanyard or strap to enable the apparatus to be worn around the neck of a user; a clip to enable the apparatus to be clipped to a belt, utility strap, or the like; a hook-and-loop connector to enable the apparatus to be attached to a mating hook-and-loop connector; or the like. Two or more connectors may be included, for example, to provide alternative connection options. The container may be configured to be disposable and replaceable. Alternatively, the apparatus may be configured to be re-usable to minimize waste.

The container may be configured with a stainless steel tube containing sodium-potassium eutectic alloy in liquid form (NaK), which absorbs heat generated during the reaction. The stainless steel tube may be present as a straight tube, such as the stainless steel tube (5) in FIG. 1B, or may be present as a coil, which is capable of absorbing more heat than the straight tube. The stainless steel tube may have a diameter of about 6 mm to about 8 mm. Furthermore, the stainless steel tube may have thin walls having a thickness of about 1 mm. The length of the stainless steel tube may vary depending on the size of the container. For example, the stainless steel tube may have a length of from about 100 mm to about 150 mm. The stainless steel tube may extend from about the top to about the bottom of the container.

The apparatus may include one or more valves that generally help to regulate air and/or oxygen flow. For example, the apparatus may include at least one valve, located in the flow path between the mask or mouthpiece and the container, to regulate air and/or oxygen flow. Although not limited to any particular valve design, a master turn-type valve (such as a knob) is preferred, in view of its ease of use. Other valve designs may also be used, such as sliding valves, pressure valves, lever valves, combinations of intake, output, and check valves, and the like. In one particular embodiment, the valve includes a polymeric knob that may be easily turned on and off as needed to regulate the flow of air and/or oxygen. Such a valve type is easy for a user to operate, and the polymeric construction of the knob helps to reduce heat transfer from the container to the knob.

The apparatus may include a mask or mouth piece that is in fluid communication with the container so that oxygen generated in the container is delivered to the mask or mouth piece. The mask may be designed to fit snugly over the nose and the mouth of the person wearing the mask, such as the mask (11) illustrated in FIG. 2C. In various other embodiments, the mask may be a full mask that covers the eyes, such as the mask (6) illustrated in FIG. 2B. Masks for such uses are well known in the art, and can be readily adapted for use with the disclosed apparatus. In various other embodiments, a mouth piece may be used in combination with a nose clip, such as the mouth piece (7) and nose clip (9) illustrated in FIG. 2A. A mouth piece may be used in combination with a bellows or a bag having a relief valve, such as the mouth piece (7) and the bag (9) and relief valve (10) illustrated in FIG. 2A. The mouth piece (7) may be fitted with a removable plug (8). The mouth piece (7) or mask (6) may be configured with a hollow tube (14) in fluid communication with the container, so that oxygen generated in the container flows from the container through the tube (14) to the mouth piece (7) or mask (6). The tube may be directly connected to the container, or to some intervening structure between the container and the tube, such as the aforementioned bellows or bag.

The potassium super oxide oxygen generating apparatus container or tank may be configured to weigh between about 250 g and 750 g, and may generate about 10 to 30 minutes of emergency oxygen, depending on the amount of super oxide present in the container and the amount of exertion by the user. In some embodiments, an oxygen-generating reaction can generate up to 100 to 120° C. In some embodiments, the apparatus may include an NaK alloy tube and a bellows or bag with a relief valve, which in combination can cool breathable air to about 30° C. or to less than 30° C.

The term "potassium super oxide" encompasses pure potassium superoxide ($KO_2$), or mixtures comprising $KO_2$ and at least one of potassium monoxide ($K_2O$) and potassium peroxide ($K_2O_2$), where $KO_2$ is present in an amount of from about 90 to about 99.9 wt % of the total weight of the potassium super oxide, such as from about 90 to about 95 Wt %, or from about 93 to about 98 wt %, or from about 94 to 96 wt %. The potassium super oxide may be in the fowl of, for example, pellets, granules, or one or more laminated sheets.

To generate 10 to 30 minutes of emergency oxygen, the container should have an interior volume in a range of from at least about 400 to about 600 ml, which accommodates between about 300 to about 500 g of potassium super oxide granules. Of course, lesser amounts of potassium super oxide can be used for smaller or shorter-use containers, such as amounts ranging from about 50 to about 300 g, and greater amounts of potassium super oxide can be used for larger or longer-use containers, such as amounts ranging from about 500 g or more. In a hand-held device, it is preferred that the container be of a size limited to an interior volume of about 500 ml or less. Containers having an interior volume of greater than 500 ml may be too cumbersome to be conveniently used as hand-held units, and may require that the user clip the apparatus to a belt or hang the apparatus around the neck using a neck strap.

The container may optionally contain graphite or carbon to help regulate moisture absorption and reduce the exotherm. The graphite or carbon may be in the form of, for example, graphite or carbon fiber fabric(s). For example, FIG. 1 illustrates a container (2) containing graphite or carbon fiber fabrics (4). The thickness of the graphite or carbon fiber fabric(s) may range, for example, from about 1 mm to about 6 mm. The graphite and carbon fiber fabric(s) eliminate the need for a screen by acting as a filter to prevent the passage of any $KO_2$ dust particles. The container may contain anhydrous LiOH to help regulate moisture absorption and reduce the exotherm.

In some embodiments, graphite or carbon fiber fabric(s) may be layered between every 25 min to 75 mm of potassium super oxide, present as a pellet(s), a granule(s) or a laminated sheet(s). In some other embodiments, the potassium super oxide may be present in the form of sheets, and the graphite or carbon fiber fabric(s) may be placed on the bottom and around the inside of the cylinder.

An inhale valve filter (13) may also be fitted over the inhale valve (12) to prevent the passage of particles as small as 10 μm in diameter from passing through. Suitable filter materials for the inhale valve filter include fiber glass, carbon, graphite, polypropylene, nylon, dacron, polyurethane, and foam rubber. The filter material may be configured as a fine screen or like a felt-type fabric, although any other configuration known in the art may be used.

The filter material may be treated with certain food grade acids to produce a treated filter that is sufficiently acidic to chemically neutralize any KOH and $KO_2$ particles contacting it, including those that are smaller than 10 μm in diameter. Thus, any particles that do pass through the filter become a neutral food grade potassium compound. The filter material may be treated, for example, by first soaking it in a solution of the food grade acid, and then vacuum evaporating the water or impregnating the acids directly into the fiber.

Suitable food grade acids include: citric acid, malic acid, fumaric acid, tartaric acid, acetic acid, ascorbic acid, boric acid, edta, erythorbic acid, gluconic acid, hydrochloric acid, phosporic acid, meta-phosphoric acid, phosphorous acid, sulfuric acid, propionic acid, levulinic acid, tannic acid, glutamic acid, nicotinic acid, perchloric acid, and mixtures thereof.

When a graphite filter material is used for the inhale valve filter, the graphite filter material is able to neutralize any KOH and $KO_2$ particles contacting it, including those that are smaller than 10 μm in diameter, without the need of any neutralizing agents.

The apparatus may be configured with the graphite or carbon fiber fabric(s), the inhale valve filter, or both.

The container may contain one or more catalysts, adjuvants, and/or initiators. The catalysts may be, for example, one or more of $NaO_2$, $Na_2O$, $Na_2O_2$, $Ca_2O_2$, $Ba_2O_2$, $Li_2O_2$, oxides of rubidium, and oxides of cesium. In some embodiments, the catalyst is preferably selected from $NaO_2$ and $Na_2O_2$. The catalyst may serve to reduce the amount of heat produced by the oxygen-generating reaction, and may slow down the reaction time. The initiator may be, for example, one or more of copper oxychloride, $CuCl_2$, and CuCl. The amount of initiator present in the container may be, for example, from about 0.25% to 1.0% of the total weight of chemical compounds in the container. The amount of the one or more catalysts, adjuvants, and/or initiators present in the container may be, for example, from about 5% to 10% of the total weight of chemical compounds in the container. The ratio of the amount of the one or more catalysts, adjuvants, and/or initiators to the amount of potassium super oxide may be, for example, about 10:90.

The above-described oxygen generating apparatus offers many benefits over conventional pressurized oxygen generators. For example, the components used in the above-described oxygen generating apparatus are non-hazardous and leak-proof, containing no compressed gas, opening the possibility for use as an emergency breathing apparatus on commercial airplanes. Furthermore, for example, the light-weight components and the slowed heat generation of the above-described oxygen generating apparatus allows it to be used for various hand-held or portable uses. In particular, the above-described oxygen generating apparatus may be useful as an emergency breathing apparatus for escaping fires, as an oxygen supplement for athletes (including skiers and mountain climbers), and as a treatment for various health conditions (including asthma, emphysema, and altitude sickness). Still further, for example, the above-described oxygen generating apparatus offers the advantage of being light-weight, disposable, and replaceable.

While this invention has been described in conjunction with the embodiments set forth above, it is evident that many alternatives, modifications and variations will be apparent to those skilled in the art. Accordingly, the embodiments of the invention set forth above are intended to be illustrative and not limiting. Various changes may be made without departing from the spirit and the scope of the disclosure as defined in the following claims.

What is claimed is:

1. An oxygen generating apparatus, comprising:

a container containing potassium super oxide;

an inhale valve; and an inhale valve filter between the potassium super oxide and the inhale valve, the filter being configured to:
prevent particles having a diameter of 10 μm from passing through the filter, and
neutralize KOH and $KO_2$ particles having a diameter of less than 10 μm that contact the filter into a food grade compound.

2. The oxygen generating apparatus of claim 1, wherein the potassium super oxide is present in an amount of about 150 g to about 500 g.

3. The oxygen generating apparatus of claim 1, wherein the potassium super oxide is present as one or more pellets, one or more granules, or one or more laminated sheets.

4. The oxygen generating apparatus of claim 1, wherein the inhale valve filter comprises a filter material selected from the group consisting of fiber glass, carbon, graphite, polypropylene, nylon, dacron, polyurethane, and foam rubber.

5. The oxygen generating apparatus of claim 4, wherein the filter material has been treated with a food grade acid selected from the group consisting of citric acid, malic acid, fumaric acid, tartaric acid, acetic acid, ascorbic acid, boric acid, EDTA, erythorbic acid, gluconic acid, hydrochloric acid, phosporic acid, meta-phosphoric acid, phosphorous acid, sulfuric acid, propionic acid, levulinic acid, tannic acid, glutamic acid, nicotinic acid, perchloric acid, and mixtures thereof.

6. The oxygen generating apparatus of claim 1, further comprising a graphite or carbon fiber fabric layered between portions of the potassium super oxide.

7. The oxygen generating apparatus of claim 6, wherein the graphite or carbon fiber fabric is about 1 mm to about 6 mm thick.

8. The oxygen generating apparatus of claim 1, further comprising a mask or mouth piece in fluid communication with the container.

9. The oxygen generating apparatus of claim 1, further comprising a catalyst selected from the group consisting of $NaO_2$, $Na_2O_2$, $Ca_2O_2$, $Ba_2O_2$, $Li_2O_2$, anhydrous LiOH, and mixtures thereof.

10. The oxygen generating apparatus of claim 1, wherein the container is made of aluminum, and an interior surface of the container is coated with polytetrafluoroethylene (PTFE) or an inert polymer.

11. The oxygen generating apparatus of claim 1, wherein an exterior surface of the container comprises a jacket comprising an insulant.

12. The oxygen generating apparatus of claim 11, wherein the jacket comprises silicone rubber.

13. The oxygen generating apparatus of claim 11, wherein the jacket comprises an inner surface or an outer surface that is ribbed.

14. The oxygen generating apparatus of claim 8, wherein the mouth piece is configured with a removable plug.

15. The oxygen generating apparatus of claim 10, wherein the interior surface is coated with PTFE, polyethylene, or polypropylene.

16. The oxygen generating apparatus of claim 1, wherein the container contains a stainless steel tube enclosed inside of the container, the stainless steel tube containing an alloy of sodium-potassium enclosed inside of the stainless steel tube.

17. The oxygen generating apparatus of claim 16, wherein the stainless steel tube has a diameter of about 6 mm and a length of about 100 mm to about 150 mm.

18. The oxygen generating apparatus of claim 1, wherein the container has an interior volume in a range of from about 400 to about 600 ml.

19. The oxygen generating apparatus of claim 1, wherein the apparatus weighs about 250 g to about 500 g.

20. An oxygen generating apparatus, comprising:
an aluminum container containing potassium super oxide, an interior surface of the container being coated with polytetrafluoroethylene (PTFE);
an inhale valve; and
an inhale valve filter between the potassium super oxide and the inhale valve, the filter being configured to:
prevent particles having a diameter of 10 μm from passing through the filter, and
neutralize KOH and $KO_2$ particles having a diameter of less than 10 μm that contact the filter into a food grade compound;
wherein the inhale valve filter comprises a filter material that has been treated with a food grade acid selected from the group consisting of citric acid, malic acid, fumaric acid, tartaric acid, acetic acid, ascorbic acid, boric acid, EDTA, erythorbic acid, gluconic acid, hydrochloric acid, phosporic acid, meta-phosphoric acid, phosphorous acid, sulfuric acid, propionic acid, levulinic acid, tannic acid, glutamic acid, nicotinic acid, perchloric acid, and mixtures thereof.

* * * * *